US006565877B1

(12) United States Patent
Mukherji et al.

(10) Patent No.: US 6,565,877 B1
(45) Date of Patent: May 20, 2003

(54) TASTE MASKED COMPOSITIONS

(75) Inventors: Gour Mukherji, Gurgaon (IN); Sandhya Goel, New Delhi (IN); Vinod Kumar Arora, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/587,535

(22) Filed: Jun. 5, 2000

(30) Foreign Application Priority Data

Jun. 11, 1999 (IN) ......................... 867/DEL/99

(51) Int. Cl.$^7$ ............................. A61K 9/14; A61K 9/16; A61K 9/20
(52) U.S. Cl. ................. 424/441; 424/464; 424/465; 424/486; 424/487; 424/488; 424/489; 424/490; 514/772.3; 514/777; 514/778; 514/782; 514/781; 514/974
(58) Field of Search ................. 424/489, 490, 424/464, 465, 441, 484, 486, 487, 488

(56) References Cited

U.S. PATENT DOCUMENTS

| 3,962,419 A | 6/1976 | Mayama et al. ............... 424/78 |
| 4,808,411 A | 2/1989 | Lu et al. ...................... 424/441 |
| 4,865,851 A | 9/1989 | James et al. ................. 424/498 |
| 4,897,270 A | 1/1990 | Deutsch et al. ............. 424/465 |
| 5,175,003 A | 12/1992 | Goldman ..................... 424/484 |
| 5,273,760 A | 12/1993 | Oshlack et al. ............. 424/480 |
| 5,286,489 A | 2/1994 | Tsau et al. ................... 424/440 |
| 5,286,493 A | 2/1994 | Oshlack et al. ............. 424/468 |
| 5,409,711 A | 4/1995 | Mapelli et al. |
| 5,580,578 A | 12/1996 | Oshlack et al. ............. 424/468 |
| 5,639,476 A | 6/1997 | Oshlack et al. ............. 424/468 |
| 5,707,646 A | 1/1998 | Yajima et al. |
| 5,958,459 A | 9/1999 | Chasin et al. ............... 424/490 |
| 5,972,373 A | 10/1999 | Yajima et al. |

FOREIGN PATENT DOCUMENTS

| IN | PCT/IB99/01735 | 10/1999 |
| WO | 97/16174 | 5/1997 |
| WO | 98/11879 | 3/1998 |
| WO | 98/18454 | 5/1998 |
| WO | 00/56266 | 9/2000 |

OTHER PUBLICATIONS

Rudolf Voight, Pharmaceutical Technology for Students and Practitioners, Ullstein Mosby GmbH & Co. KG, Berlin [Germany], 1993 Translation from German to English.

Primary Examiner—James M. Spear
(74) Attorney, Agent, or Firm—Jayadeep R. Deshmukh, Esq.

(57) ABSTRACT

A taste masked composition which comprises a bitter tasting drug, a combination of two enteric polymers comprising, a methacrylic acid copolymer and a phthalate polymer is described. The composition of the present invention is prepared by dissolving the active ingredient, the methacrylic acid copolymer and the phthalate polymer in a solvent and recovering the composition from the solution thereof.

25 Claims, No Drawings

TASTE MASKED COMPOSITIONS

FIELD OF INVENTION

The present invention relates to taste masked compositions for bitter drugs, comprising a combination of two enteric polymers, such as a methacrylic acid copolymer, and a phthalate polymer. It also relates to a process for preparing such a composition.

BACKGROUND OF THE INVENTION

For ease and safety of administration, most drugs are formulated as tablets or capsules for oral administration. However, patients at the extremes of age, such as children and the elderly, often experience difficulty in swallowing solid oral dosage forms. For these patients, drugs are commonly provided in liquid dosage forms such as solutions, emulsions and suspensions. These dosage forms usually permit perceptible exposure of the active drug ingredient to the taste buds, which can be a problem when the drugs have an unpleasant taste or are extremely bitter. Conventional taste masking techniques such as the use of sweeteners, amino acids and flavoring agents are often unsuccessful in masking the taste of highly bitter drugs and other techniques have been and continue to be exploited for the effective taste masking of such drugs. Extremely bitter drugs, like, quinine, ciprofloxacin, clarithromycin, cefuroxime axetil, can now be formulated as a fairly acceptable range of products even for pediatric use, which through conventional techniques would be impossible to formulate.

Use of cation—exchange resins (such as polysulfonic acid and polycarboxylic acid polymers) to adsorb amine drugs for taste masking and sustained release has been reported to have limited applicability and is not capable of masking the taste of highly bitter drugs. Coating of bitter drugs is another method which has been reported for taste masking. This technique alone may prove effective for moderately bitter drugs or in products where the coated particles are formulated as aqueous preparations before administration or are formulated in a non-aqueous medium. This technique has its limitations as coating of fine particles is usually technology intensive and coated granules are readily ruptured by chewing and compression.

Lipid-based microencapsulation is another technique used to taste mask the drugs. This technique requires highly sophisticated hot-melt granulation for producing fine particles, and may have adverse effects on heat sensitive molecules or restrict drug release adversely. U.S. Pat. No. 4,865,851 describes cefuroxime axetil in particulate form coated with an integral coating of lipid or a mixture of lipids.

U.S. Pat. No. 4,808,411 describes a taste-masked composition comprising 95% of erythromycin or a derivative thereof and about 5 to about 75% of a carbomer. The drug and carbomer are believed to be held together by both the ionic interactions between the amine group of erythromycin compound and the carbonyl group of the carbomer and by the gel properties of the carbomer. This complex is further taste masked by coating. Although use of this complexing technique, optionally with a coating, has evolved into a useful technique for taste-masking, proper selection of the complexing agent is vital such that in trying to achieve taste-masking, drug release is not compromised.

U.S. Pat. No. 5,286,489 describes a porous drug-polymer matrix formed by admixing one or more bitter tasting active ingredient and a methyl methacrylic ester copolymer in at least a 1:1 by weight ratio of active ingredient to copolymer, effective to mask the taste of the drug. None of the examples described in this patent disclose the effect of these polymers on the release of the drug from the matrix. It has been our experience that although the drug-polymer matrix formed following the teachings of this patent results in good taste-masking, it also retards the rate of drug release from the matrix to an extent which would be unacceptable for a conventional immediate release formulation. Following the teachings of this patent, only 42% of cefuroxime axetil was released from the matrix in 45 minutes in media of pH greater than 4.0. The matrix described in this patent is therefore unsuitable for drugs which are absorbed at a pH range greater than 4.0. To enhance the release of the drug, an enteric phthalate polymer was added into the matrix without significantly compromising on the taste masking.

Accordingly, none of the references heretofore described is completely satisfactory for various reasons.

SUMMARY OF THE INVENTION

The object of the present invention is to provide a taste masked composition, which effectively masks the taste of the drug without compromising the dissolution rate, comprising a bitter tasting drug and a combination of two enteric polymers comprising a methacrylic acid copolymer and a phthalate polymer.

A further object of the present invention is to describe a process for the preparation of a taste masked matrix comprising the process of dissolving the bitter tasting drug, a methacrylic acid copolymer and a phthalate polymer, in a suitable organic solvent followed by the recovery of said taste masked matrix from the solution thereof.

DETAILED DESCRIPTION OF THE INVENTION

The taste masked composition of the present invention comprises a bitter tasting active, and two enteric polymers wherein the enteric polymers are a methacrylic acid copolymer and a phthalate polymer. Examples of bitter or unpleasant tasting drugs which may be used, include, but are not limited to, macrolide antibiotics, such as erythromycin and clarithromycin, fluoroquinolones such as ciprofloxacin and norfloxacin, cephalosporins such as cefuroxime and ceftriaxone, tetracyclic antibiotics like chloramphenicol, chlorpromazine etc. The drug itself or its pharmaceutically acceptable salt or ester may be used in the present invention.

The methacrylic acid copolymers used according to the present invention, may include methylmethacrylic ester copolymers, such as Eudragit S and Eudragit L (trademark of Rohm Pharma) and copolymers of ethyl acrylate and methacrylic acid as Eudragit L-100-55 (trademark of Rohm Pharma). The phthalate polymers include cellulose acetate phthalate, ethyl vinyl phthalate, polyvinyl acetate phthalate and hydroxy alkyl cellulose phthalates. This combination of the two enteric polymers, methacrylic acid copolymer and a phthalate polymer results in optimal taste-masking and dissolution characteristics of the drug. The ratio of methacrylic acid copolymer to phthalate polymer can be varied from 1:9 to 9:1 depending upon intensity of bitterness and desired release of the active ingredient. Most preferably the two polymers are in the ratio of 1:1.

Preferably for optimal taste masking effect, total polymer to drug ratio is at least 1:4.

According to the present invention, the taste masked matrix described above, is prepared by dissolving, optionally with heating, the bitter active ingredient, a methacrylic acid copolymer and a phthalate polymer in a solvent system and then recovering the matrix including the active ingredient and the two polymers from the solution thereof. The solvent system chosen is one in which, both the active ingredient and the polymers are either soluble or swellable. Preferred solvents include water, ketones such as acetone, alcohols such as ethanol, esters such as ethyl acetate and their mixtures. The matrix is recovered by conventional methods which include vacuums evaporation, tray drying, spray drying, and drum or belt film drying. Spray drying is the preferred method for solvent removal. The "solid solutions" thus formed keep the drug in a finely dispersed state within the polymers, preventing the exposure of the bitter tasting drug to the taste buds.

The process of spray drying gives highly porous material which can be further compacted to granules to improve the taste masking effect. The porosity of the granules thus obtained, is not only important for dissolution but also determines the extent of taste masking.

Channeling agents can be used to further tailor the drug release from the compacted granules. Channeling agents help in opening up the granules in a specific media as desired. The channeling agents include, disintegrants like croscarmellose sodium, crospovidone and sodium starch glycolate, diluents such as lactose, mannitol, sodium chloride, talc, polyvinyl pyrrolidone; gelling agents like carbopol, and xanthan gum, among others.

The taste masked granules obtained may be mixed with flavoring agents such as natural or artificial flavors, citric and tartaric acids, sweeteners such as saccharin and aspartame, and with other pharmaceutically acceptable excipients to be formulated as conventional whole, chewable or disperseible tablets, dry syrups, suspensions, sachets or any other suitable oral dosage forms.

The use of particle coating offers additional taste masking on the product. The coating composition can be constituted of either pH dependent or pH independent polymers depending on desired product characteristics. Coating compositions such as that described in our PCT application No. PCT/IB99/01735 (which is incorporated herein by reference) offer additional advantages as they can effectively mask the remaining bitterness of the drug without significantly affecting its dissolution profile. Other coating polymers such as the cellulosic polymers and methacrylic acid copolymers may also be used to optimize the taste masking effect.

The examples given herein further illustrate the effectiveness of our formulation in achieving both taste-masking and optimal dissolution of the drug from the matrix.

EXAMPLE 1

2 g of cefuroxime axetil was taken together with 2 g polymer mixture (0.7:0.3, Eudragit L100-55: hydroxypropyl methyl cellulose phthalate) and dissolved in acetone (20 ml) containing 5% water. The resulting mixture was tray dried and sized to obtain BSS mesh 44/85 particles. These granules showed adequate taste masking and 95% of the drug was released from the matrix within 45 minutes in pH 6.8 phosphate buffer.

EXAMPLE 2

20 g cefuroxime axetil and 40 g total polymer (1.2:0.8 w/w mixture of Eudragit L-100-55 and hydroxypropyl methyl cellulose phthalate) were dissolved in 112 ml acetone and 16 ml water mixture. The solvent was removed by tray drying under vacuum at 40° C. for 12 hours. The dried mass was milled to get a BSS mesh 44/85 size fraction. The granules thus obtained showed adequate taste masking and released 100% of the drug in 45 minutes in pH 6.8 phosphate buffer.

EXAMPLE 3

60 g cefuroxime axetil and 60 g total polymer (1:1 w/w mixture of Eudragit L-100-55 and hydroxypropyl methyl cellulose phthalate) were dissolved under stirring in a mixture of 875 ml acetone and 125 ml water at 35–40° C. The solvent was removed by spray drying. The spray dried material was further dried for 12 hours at 40° C. under vacuum to obtain a fluffy and amorphous material. This spray dried material was compacted and milled to obtain granules of the desired particle size and taste (BSS mesh 44/85). The granules thus obtained released 100% of the drug from the matrix within 45 minutes in pH 6.8 buffer. These granules therefore showed ideal characteristics of both taste masking and drug release from the matrix.

EXAMPLE 4

75 g clarithromycin and 75 g polymer (1:1 mixture of hydroxypropyl methyl cellulose phthalate+Eudragit L-100-55) were dissolved under stirring I in a mixture of acetone (110 ml) and water (15 ml) at 45–50° C. The solvent was removed on Buchi rotavapor and the thick viscous mass so obtained was; tray dried at 60° C. to obtain a flaky, partially taste masked material. The product thus obtained was milled to give partially taste masked granules of the desired particle size (BSS mesh 44/85).

These granules were further coated with the coating composition described in our PCT application (PCT/IB99/01735) to yield a bitterness material suitable for use in an oral suspension. These coated granules released 84% of the drug within 60 minutes in pH 6.8 phosphate buffer.

What is claimed is:

1. A taste masked composition comprising a bitter tasting drug selected from the group consisting of erythromycin, clarithromycin, ciprofloxacin, norfloxacin, cefuroxime, ceftriaxone, chlorampheniol, chloropromazine and their pharmaceutically acceptable salts and esters, and a combination of two enteric polymers comprising, a methacrylic acid copolymer and a phthalate polymer, wherein the ratio of methacrylic acid copolymer to phthalate polymer is between 1:9 or 9:1.

2. The composition as described in claim 1 wherein the methacrylic acid copolymer is selected from the group consisting of methylmethacrylic ester copolymers and copolymers of ethyl acrylate and methacrylic acid.

3. The composition as described in claim 1 wherein the phthalate polymer is selected from the group consisting of cellulose acetate phthalate, ethylvinyl phthalate, polyvinyl acetate phthalate and hydroxy alkyl cellulose phthalate.

4. The composition as described in claim 1 wherein the ratio of methacrylic acid copolymer to phthalate polymer is between 1:9 or 9:1.

5. The composition as described in claim 1 wherein the combined w/w ratio of the polymers to the drug is at least 1:4.

6. A process for the preparation of a taste masked matrix comprising dissolving the bitter tasting drug selected from the group consisting of erythromycin, clarithromycin, ciprofloxacin, norfloxacin, cefuroxime, ceftriaxone, chlorampheniol, chloropromazine and their pharmaceutically acceptable salts and esters, a methacrylic acid copolymer and phthalate polymer in a suitable organic solvent and recovering said taste masked matrix from the solution thereof.

7. The process of claim 6 wherein the dissolving happens in the presence of water.

8. A process as described in claim 6 wherein the bitter tasting drug is selected from the group consisting of macrolide antibiotics, fluoroquinolones and cephalosporins.

9. The process of claim 6 wherein the methacrylic acid copolymer is selected from the group consisting of methyl methacrylic ester copolymers and copolymers of ethyl acrylate and methacrylic acid.

10. The process of claim 6 wherein the phthalate polymer is selected from the group consisting of cellulose acetate phthalate, ethylvinyl phthalate, polyvinyl acetate phthalate and hydroxy alkyl cellulose phthalate.

11. The process of claim 6 wherein the ratio of methacrylic acid copolymer to phthalate polymer is between 1:9 to 9:1.

12. The process of claim 6 wherein the combined w/w ratio of two polymers to the drug is at least 1:4.

13. The process of claim 6 wherein the organic solvents used are selected from ketones, alcohols, esters or mixtures thereof with or without water.

14. The process of claim 6 wherein the matrix is recovered by a method, selected from the group consisting of evaporation, vacuum evaporation, tray drying, spray drying, drum and belt film drying.

15. The drying process of claim 14, wherein the dried product is compacted to granules.

16. The process of claim 14 wherein the compacted granules are coated.

17. The process of claim 13 wherein the granules are mixed with sugar or artificial sweeteners and/or flavoring agents.

18. The process of claim 15 wherein the taste masked granules are formulated as dry syrups, suspensions, conventional whole, chewable, or dispersible tablets.

19. A process for the preparation of a taste masked matrix comprising a bitter tasting drug, clarithromycin methyl methacrylic ester copolymer and hydroxypropylmethylcellulose phthalate wherein the drug clarithromycin and the two polymers areidissolved in acetone, followed by recovery of the said taste masked matrix from the solution thereof.

20. Coated taste masked granules comprising a bitter tasting drug selected from the group consisting of erythromycin, clarithromycin, ciprofloxacin, norfloxacin, cefuroxime, ceftriaxone, chlorampheniol, chloropromazine and their pharmaceutically acceptable salts and esters and a combination of two enteric polymers comprising, a methacrylic acid copolymer and a phthalate polymer, wherein the ratio of methacrylic acid copolymer to phthalate polymer is between 1:9 or 9:1.

21. The composition as described in claim 20 wherein the methacryic acid copolymer is selected from the group consisting of methylmethacrylic ester copolymers and copolymers of ethyl acrylate and methacrylic acid.

22. The composition as described in claim 20 wherein the phthalate polymer is selected from the group consisting of cellulose acetate phthalate, ethylvinyl phthalate, polyvinyl acetate phthalate and hydroxy alkyl cellulose phthalate.

23. The composition of claim 20 wherein the granules include chanelling agents selected from the group consisting of croscarniellose sodium, crospovidone, sodium starch glycolate, lactose, mannitol, sodium chloride, talc, polyvinyl pyrrolidone, carbopol, and xanthan gum.

24. The composition of claim 20 wherein the granules are mixed with sugar or artificial sweeteners and/or flavoring agents.

25. The composition of claim 20 wherein the taste masked granules are formulated as dry syrups, suspensions, conventional whole, chewable, dispersible tablets or any other suitable oral dosage form.

* * * * *

UNITED STATES PATENT AND TRADEMARK OFFICE
CERTIFICATE OF CORRECTION

PATENT NO. : 6,565,877 B1  Page 1 of 1
DATED : May 20, 2003
INVENTOR(S) : Mukherji et al.

It is certified that error appears in the above-identified patent and that said Letters Patent is hereby corrected as shown below:

<u>Column 6,</u>
Line 3, "areidissolved" should read -- are dissolved --

Signed and Sealed this

Twenty-first Day of October, 2003

JAMES E. ROGAN
*Director of the United States Patent and Trademark Office*